United States Patent [19]

Elias, deceased

[11] E Patent Number: Re. 32,957

[45] Reissued Date of Patent: Jun. 20, 1989

[54] ABSORBENT ARTICLE

[75] Inventors: Robert T. Elias, deceased, late of Downers Grove, by Donald R. Elias, executor, Westmont, both of Ill.

[73] Assignee: Johnson & Johnson, New Brunswick, N.J.

[21] Appl. No.: 729,678

[22] Filed: May 2, 1985

Related U.S. Patent Documents

Reissue of:

[64] Patent No.: 4,381,783
Issued: May 3, 1983
Appl. No.: 274,931
Filed: Jun. 18, 1981

U.S. Applications:

[63] Continuation of Ser. No. 954,152, Oct. 24, 1978, abandoned.

[51] Int. Cl.[4] ..... A61F 13/16

[52] U.S. Cl. ..... 604/368; 604/370; 604/375; 604/378

[58] Field of Search ..... 604/368, 370, 378; 428/297, 306, 308

[56] References Cited

U.S. PATENT DOCUMENTS

| | | | |
|---|---|---|---|
| 2,644,454 | 12/1950 | Morhard . | |
| 3,017,304 | 5/1956 | Burgeni . | |
| 3,121,427 | 2/1964 | Mosier | 128/285 |
| 3,344,789 | 12/1964 | Arnold et al. . | |
| 3,381,688 | 5/1965 | Satas . | |
| 3,612,055 | 10/1971 | Mesek . | |
| 3,670,731 | 6/1972 | Harmon | 604/368 |
| 3,768,480 | 10/1973 | Mesek et al. . | |
| 3,888,257 | 6/1975 | Cook . | |
| 3,900,378 | 8/1975 | Yen et al. | 128/284 |
| 3,903,889 | 9/1975 | Torr . | |
| 3,938,522 | 2/1976 | Repke . | |
| 3,965,904 | 6/1976 | Mesek et al. . | |
| 4,055,180 | 10/1977 | Karami | 604/370 |
| 4,055,184 | 10/1977 | Karami . | |
| 4,079,739 | 3/1978 | Whitehead . | |
| 4,102,340 | 7/1978 | Mesek et al. | 604/368 |
| 4,105,033 | 8/1978 | Catterjee et al. . | |
| 4,186,165 | 1/1980 | Aberson et al. . | |
| 4,232,674 | 11/1980 | Melican . | |
| 4,251,643 | 2/1981 | Harada et al. | 604/368 |

FOREIGN PATENT DOCUMENTS 489308 12/1929 Fed. Rep. of Germany .

*Primary Examiner*—John D. Yasko
*Assistant Examiner*—Sharon Rose

[57] ABSTRACT

An absorbent article, such as a disposable diaper, is disclosed which includes a moisture permeable facing layer, a backing layer, and an absorbent layer disposed between said facing and backing layers and including at least one pocket containing a uniform admixture of discrete superabsorbent particles and discrete introfying particles.

40 Claims, 3 Drawing Sheets

FIG. 1
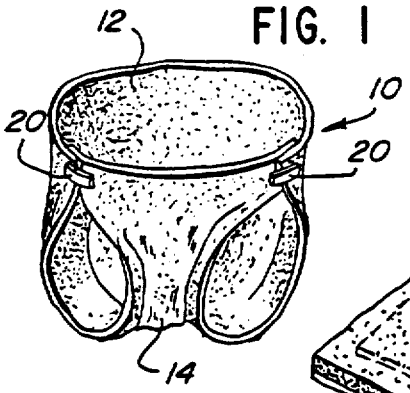
FIG. 2
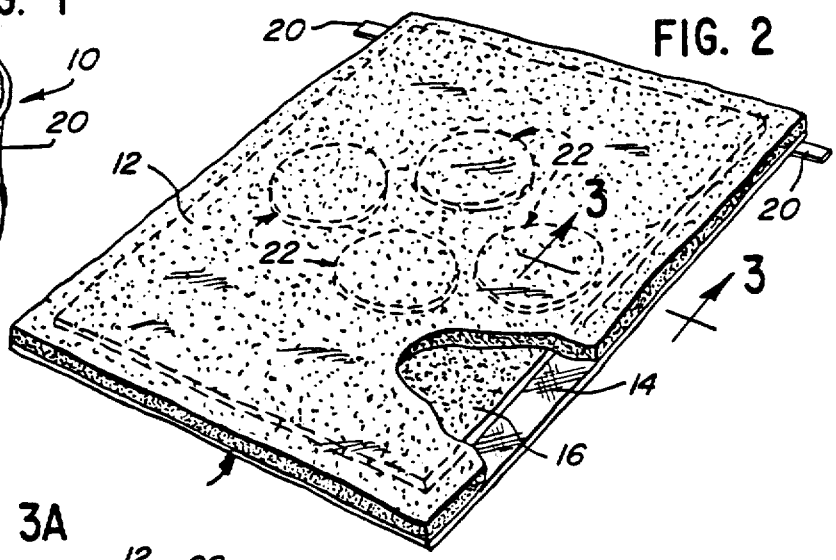
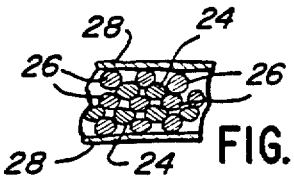
FIG. 3A
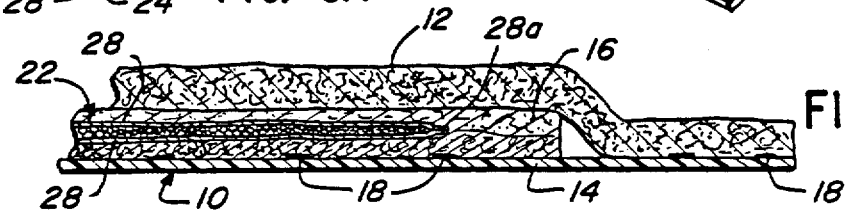
FIG. 3
FIG. 5
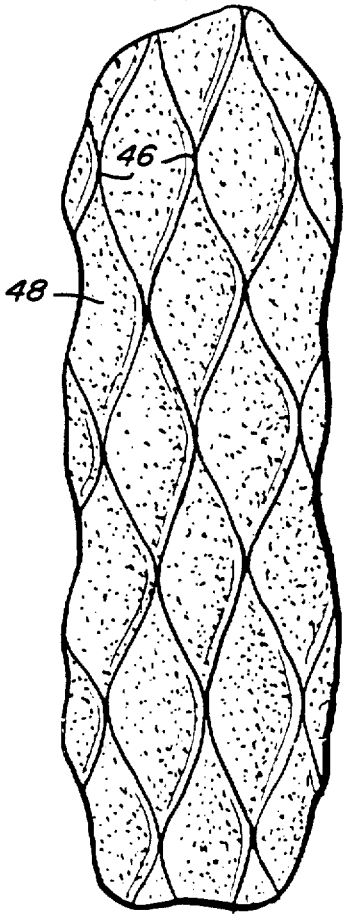
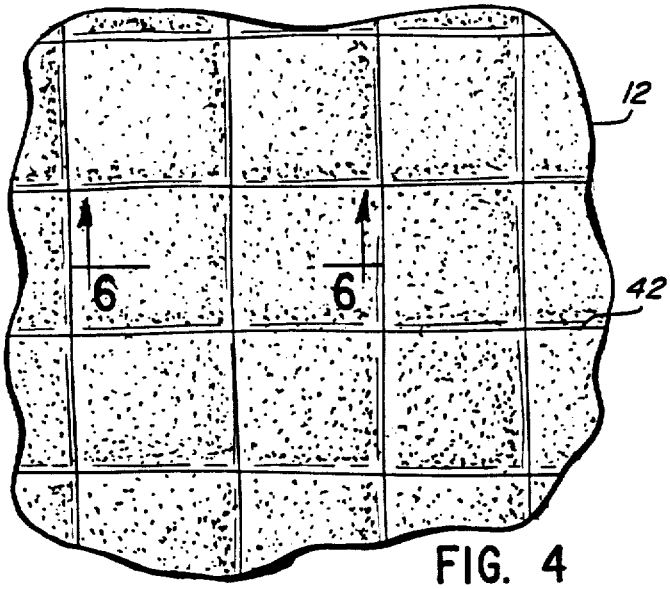
FIG. 4
FIG. 6
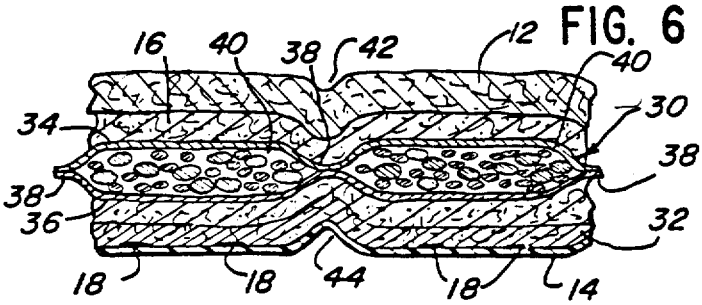

ABSORBENT ARTICLE

Matter enclosed in heavy brackets [ ] appears in the original patent but forms no part of this reissue specification; matter printed in italics indicates the additions made by reissue.

This is a continuation, of application Ser. No. 954,152, filed Oct. 24, 1978 now abandoned.

BACKGROUND OF THE INVENTION

This invention relates to an improved absorbent article and particularly to a superabsorbent disposable diaper. More particularly, this invention provides a superabsorbent batt or panel component especially desirable for use in a disposable diaper, but also having use in diverse absorbent articles such as sanitary napkins, tampons, etc.

The most common absorbent material used in disposable diapers is a mass of cellulose fibers. Although the cellulose itself will absorb some liquid, causing the fibers to swell, most of the absorbed liquid is held in the capilliary spaces among the fibers. The liquid within the cellulose fibers is difficult to remove, but the liquid held in between the fibers is removed readily by squeezing.

Much effort has been expanded to find materials which will be more cost effective than cellulose fibers with respect to liquid absorbency and retention. Typical materials and various ways of incorporating them into absorbent products are disclosed in U.S. Pat. Nos. 3,344,789, 3,683,917, 3,783,872, 3,814,101, 3,815,601, 3,886,941, 3,890,974, 3,898,143, 3,900,378, 3,901,231, 3,901,236, 3,956,224, 3,957,605, 3,963,805, 4,058,124, 4,090,013, 4,103,062, and 4,105,033.

Some of the more promising materials are in the form of granules, beads, fibers, etc. which take liquid into their respective structures resulting in swelling and becoming like a gel. These materials are called superabsorbents. superabsorbents have been placed among fibers to make absorbent pads which combine the cushioning properties and the integrity of fibrous pads with the liquid holding capacity of the superabsorbent. However, these combinations have been disappointing because the liquid holding capacity has fallen far short of the expected total for fibers and superabsorbent combined.

Perhaps these failures can be attributed to the fact that a particle of superabsorbent swells and in so doing pushes the fibers apart and occupies void space among the fibers. This void space now occupied by the superabsorbent could previously have been occupied by liquid.

The present invention provides optimum use of the superabsorbent effectiveness by confining the superabsorbent in a specially allocated space so that it does not occupy voids between the fibers.

SUMMARY OF THE INVENTION

According to the present invention, a disposable diaper or other catamenial device is provided comprising a moisture permeable facing layer, a backing layer which may be moisture impermeable, and a fibrous absorbent panel affixed between said facing and backing layers, said absorbent panel including one or more discrete pockets therein, at least a portion of each of said pockets being moisture permeable, and each of said pockets containing therewithin a plurality of discrete particles of hydrocolloid material, said particles of hydrocolloid material being retained in spaced relationship relative to one another by discrete introfying particles disposed within each pocket.

Suitable pockets can be individual cells or strips of cells or in fact multiple cells in both length and width providing a type of "quilt." Each of the discrete cells contains a mixture of a superabsorbent and introfying particles.

The particulate absorbent materials contemplated herein contain water-insoluble but water-swellable polymeric substances having at least 25 percent of their molecular structure composed of hydrophilic groups and capable of retaining water in an amount which is at least 10 times the weight of the absorbent material in dry form, and preferably about 15 to about 70 times the weight, or more.

Illustrative particulate absorbent materials that are suitable for the present purposes are powered graft copolymers of a water-isoluble polysaccharide such as starch or cellulose having hydrophilic chains of carboxyl, carboxylate-, and/or carbamide-bearing moieties.

Water-insoluble starch or a wide variety of cellulosic fibers can be utilized as starting materials for producing graft copolymers of this general type. Typical of such cellulosic fibers are: cotton, cotton linters, wood pulp, bagasse pulp, jute, rayon, and the like. The polysaccharide chains are then modified by grafting thereon a hydrophilic chain of the general formula

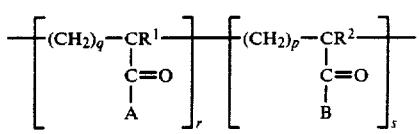

(I)

wherein A and B are selected from the group consisting of $-OR^3$, —O(alkali metal), $-OHNH_3$, $-NH_2$, wherein $R^1$, $R^2$ and $R^3$ are selected from the group consisting of hydrogen and alkyl having 1 to 4 carbon atoms, wherein r is an integer having a value of 0 to about 5000, s is an integer having a value of 0 to about 5000, r plus s is at least 500, p is an integer having a value of zero or 1, and q is an integer having a value of 1 to 4.

Preferred hydrophilic chains are hydrolyzed polyacrylonitrile chains and copolymers of polyacrylamide and sodium polyacrylate. In another preferred embodiment both ionizable polymeric moieties and non-ionizable polymeric moieties can be grafted on the same polysaccharide backbone.

While the detailed mechanism by which the grafting of the hydrophilic chain or chains onto a starch or a cellulosic backbone is not fully known, it is believed that grafting takes place through a free radical mechanism whereby the free radical is situated on the backbone which serves as a reducing agent, and the hydrophilic chain is attached to the starch or cellulosic reducing agent through a carbon linkage. The produced graft copolymer using a cellulosic backbone is of the type

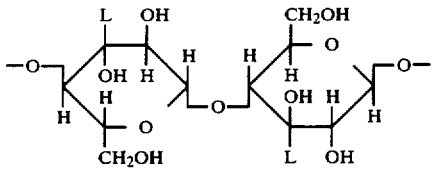

(II)

wherein L represents the hydrophilic chain of Formula I, above. The graft copolymer using a starch backbone is substantially similar to that represented by Formula I except that a starch backbone is present in lieu of a cellulosic backbone.

Also suitable as absorbents are cross-linked synthetic polymers and grafts on polysaccharides of synthetic polymers or synthetic copolymers.

A particulate material that is particularly well suited for the purposes of the present invention is Permasorb 10, a cross-linked synthetic polymer commercially available in the form of a powder from the National Starch and Chemical Corp.

The introfying particulate material is substantially inert mineral substances of a desirable particle size which enhance the impregnation of the super-absorbent with the liquid. In effect, the introfying material is a separator. In other words, it separates the hydrocolloid particles one from another. The introfying material is non-reactive, non-swellable, and crush resistant, and is a particulate material. Examples include particles of volcanic rock such as perlite, diatomaceous earth such as Celite, inorganic clay such as kaolin, and the like.

The material used to form the pockets is constructed, at least in part, of a permeable material. Typical liquid permeable materials are water-permeable paper, for example, high wet strength paper used for tea bags, non-woven fabrics, creped tissues, reticulated foam or screening, and the like. It is advantageous if the material is heat sealable for ease in formation of the pocket cell. If not, suitable adhesives or tape or other sealing means may be used. One suitable water-permeable paper is a product of the Dexter Corporation, Windsor Locks, Conn., identified as Grade 1234. It is a high quality, two phase teabag paper made from a blend of manila hemp and cellulose fibers in one phase and an integral layer of heat sealable thermoplastic fibers in the other phase.

The disposable diaper of the present invention comprises a moisture permeable facing layer, a moisture impermeable backing layer, and an absorbent panel containing the pockets discussed above, sandwiched between the facing and backing. Each pocket contains a substantially uniform admixture of hydrocolloid particulate material and introfying particles.

Several different types of facing materials may be used for the diaper facing sheet. For example, the facing sheet may be made up of a mixture of fibers consisting predominantly of inexpensive short cellulosic fibers such as wood pulp fibers or cotton linters, in amounts of about 75% to about 98%, the balance being textile length fibers such as rayon as described in U.S. Pat. No. 3,633,348 to Liloia et al.

Facing sheet materials suitable for use in this invention can have fabric weight in the range of about 1 to 5 oz./yd.$^2$ and densities of less than 0.15 g./cc. generally in the range between 0.05 and 0.1 g./cc. The dry strength of the facing sheet for a fabric having a weight of about 1.5 oz./yd$^2$ is at least 0.15 lbs./in. of width in the machine direction and at least 0.1 lbs./in. of width in the cross direction. Such fabrics have unusually good elongation, loft, softness and drape characteristics in comparison to prior products incorporating any substantial amount of short fibers.

The facing sheet may also be made of an apertured, non-woven fabric which is formed, for example, in accordance with the teachings of commonly assigned U.S. Pat. Nos. 2,862,251; 3,081,514 and 3,081,515. Briefly, such fabrics are foraminous structures wherein groups or groupings of fibers have been rearranged from a fibrous nonwoven starting web into positions surrounding less dense fabric portions by passage of a fluid through the starting material. The fibers within the groupings are mechanically interlocked, and may be arranged into various patterns, as is well known by those skilled in the art. A suitable binder may be utilized to help retain the fibers in their rearranged locations, as is also well known by those skilled in the art. The fabric can be made of naturally occurring fibers, synthetic fibers, or blends thereof. Typical facing sheets made of a polyester type material can have a weight of about 0.75 oz./yd.$^2$.

In addition, the facing sheet can be formed of a non-apertured material, such as a nonwoven isotropic web, or the like. In all of the aforementioned facing materials, the material should be relatively hydrophobic so as to retard wicking within the facing layer.

The highly moisture-absorbent fibrous pad or batt, which usually is substantially rectangular in shape but smaller than the facing sheet and the backing sheet, can be formed in accordance with the teachings of U.S. Pat. No. 3,612,055 to Mesek et al. If desired, a highly moisture-absorbent layer can be provided substantially coextensive with backing sheet and facing sheet.

A suitable backing sheet material for the diapers embodying the present invention can be an opaque polyethylene web about 0.001 inch thick. Another suitable material for this purpose is a polyethylene terephthalate web having a thickness of about 0.005 inch. Typical disposable diapers which can be fitted with tab-type adhesive fasteners described hereinabove are shown in U.S. Pat. No. 3,612,055 to Mesek et al. and U.S. Pat. No. 3,683,916 to Mesek et al.

The absorbent panel is also identified as an absorbent batt.

The body of the batt is substantially more wettable than the facing layer and tends to draw liquid away from the facing layer. The individual fibers of the batt are extremely wettable, generally having liquid-fiber contact angles below about 15° and approaching zero in the optimum embodiment, as described in detail in the above-mentioned application. The wickability, or preferential absorptivity of the body of the batt for water is limited, however, by its low density which results in a large effective capillary radius for the capillaries between adjacent fibers.

The pressure causing a liquid to enter a cylindrical capillary is expressed by the equation:

$$P=(2\gamma \cos \theta)/r$$

wherein

P is a capillary pressure, $\gamma$ is the surface tension of the liquid, $\theta$ is the liquid-fiber contact angle, and r is the capillary radius.

With a given liquid, the pressure (capillary force) increases with the cosine of the liquid-fiber contact angle (reaching a maximum where the angle is zero), and decreases with narrower capillary radii so that narrower capillaries will draw liquid from wider ones.

The relative wickability between the facing layer and the body of the batt is affected by both the relative densities of the layers and the relative wettability of the individual fibers in each layer. The facing layer is sometimes more dense than the body of the batt, tending to provide greater wickability in the facing layer, but even then the individual fibers of the batt have substantially smaller liquid-fiber contact angles than those of the facing layer, overcoming the density difference and providing a substantial overall increase in capillary pressure to absorb liquid into the body of the batt.

A densified fiber layer of the batt is formed on the surface which contacts the backing. It provides the maximum capillary pressure because it combines the very low contact angle of the fibers of the batt with the high density (small capillary radius) of the densified fibers.

When urine is voided into an area in the facing layer, it partially wets the facing layer and is absorbed therein, spreading out to a limited extent to form a roughly circular wetted zone therein. When the urine passes through the facing layer and comes into contact with the body of the batt, it is preferentially absorbed into the body of the batt because of the enhanced wettability thereof. It spreads within the body of the batt to wet a roughly circular zone therein that is slightly larger than the wetted zone in the facing layer.

The urine is transported relatively rapidly in all directions of the densified layer because the densified layer is continuous over one face of the absorbent panel.

On occasions when a substantial amount of urine has been voided, the densified layer becomes saturated and excess urine, aided by the presence of the impervious sheet and its adherence to the densified layer in a discontinuous pattern substantially throughout the interface therebetween, flows into the previously dry portions of the body of the batt, and finally into the previously dry portions of the facing layer. It is to be noted, however, that such flow from a saturated densified layer is from the outermost portions of the diaper inward so that most of the facing layer remains dry until all other fibrous portions of the diaper are saturated.

The densified layer of the batt, for the reasons explained above, creates a high capillary pressure which tends to move liquid away rapidly from the area of the original wetting. However, the speed of liquid migration in terms of volume per unit time is limited in the densified layer because of the resistance provided by its small capillaries.

In accordance with the present invention a substantially uniform admixture of a superabsorbent in particulate form and introfying particulate material are provided in one or more pockets in the absorbent panel of a disposable diaper. The admixture is placed in the pockets in a portion such that when the superabsorbent swells there is adequate space in the enclosed pocket to retain the swollen substance. The pockets can be placed in the absorbent panel between the densified layer and the rest of the panel. They may also be placed between the densified layer and the liquid impervious backing layer. In a preferred embodiment, a section of the absorbent panel is cut out and the pocket or pockets of the admixture are placed in the cut-out space.

While the size of the introfying particles is not critical to the present invention, it is preferred that they be no larger than the hydrocolloid particles. And, for purposes of the present invention, the introfying particles need not be of uniform size or shape. However, it is important that the introfying particles be blended in a uniform admixture with the hydrocolloid particles, and that the admixture have a bulk volume that is substantially greater than the bulk volume of the hydrocolloid particles themselves. In this regard, it is preferred that the admixture have a bulk volume that is from about 4 to about 60 times as great as the bulk volume of the hydrocolloid particles therein, with the most preferred admixture-hydrocolloid range being from about 20 to about 50. Bulk volume ratios of the type contemplated herein not only provide the desired spacing for the hydrocolloid particles, but also provide room for expansion of the hydrocolloid particles when they are wetted to capacity. Bulk volumes of the particulate materials may be measured by placing the particulate material in a graduated cylinder and shaking or vibrating it until constant volume is obtained.

In a specific example, when Permasorb 10, mentioned above, is the hydrocolloid and Celite FC (a diatomaceous earth commercially available from Johns-Manville Corp.) is the introfying particle, an admixture of equal weights of the two materials produces a total bulk volume which is about 4.6 times the bulk volume of the hydrocolloid particles therein, and an increase of the weight proportion of the Celite FC particles to six times the weight of the hydrocolloid particles produces a total bulk volume which is about 23.8 times the bulk volume of the hydrocolloid particles therein.

With a preferred introfying particle, such as perlite, which has a bulk density less than about 0.05 g./ml., the increase in bulk volume is substantially greater. A mixture of 2 parts by weight of perlite per part of Permasorb 10 produces a bulk volume which is about 22.8 times the bulk volume of hydrocolloid particles therein; and a mixture of 5 parts by weight of perlite per part of Permasorb 10 produces a bulk volume which is about 49.1 times as great as the bulk volume of the hydrocolloid particles therein.

When hydrocolloid particles of the type contemplated herein are blended with introfying particles of the type set forth above in bulk volume ratios as described above, the introfying particles cooperate to maintain the hydrocolloid particles in spaced relationship thereby preserving the interstitial network between the hydrocolloid particles and permitting liquid to circulate through the void areas and contact the exposed surfaces of all of the hydrocolloid particles. The introfying particles prevent adjacent hydrocolloid particles from coalescing when they are wetted and begin to swell, thereby maximizing utilization of the large absorptive capacity of the hydrocolloid particles. And, since the admixture is confined with one or more discrete pockets in the absorbent layer of the absorbent product, the swelling hydrocolloid particles do not expand in the void areas in the adjacent fibrous portion of the absorbent layer so that the capillary network of the fibrous portion is not impaired.

While, as noted above, the inventive concept of the present application has applicability to a wide variety of absorbent products, a disposable diaper is illustrated in the accompanying drawings, in which:

FIG. 1 is a perspective view of a diaper in the configuration assumed after the diaper is placed on an infant;

FIG. 2 is an enlarged perspective view of the diaper of FIG. 1 laid out flat, with a portion broken away for clarity of illustration;

FIG. 3 is a cross-sectional view taken generally along line 3—3 of FIG. 2;

FIG. 3A is an enlarged cross-sectional view through one of the discrete pockets of the present invention containing a uniform admixture of hydrocolloid and introfying particles;

FIGS. 4 and 5 are enlarged plan views showing further embodiments of the invention; and FIG. 6 is a cross-sectional view taken generally along line 6—6 of FIG. 4;

DESCRIPTION OF ILLUSTRATED EMBODIMENTS

Figure 7:
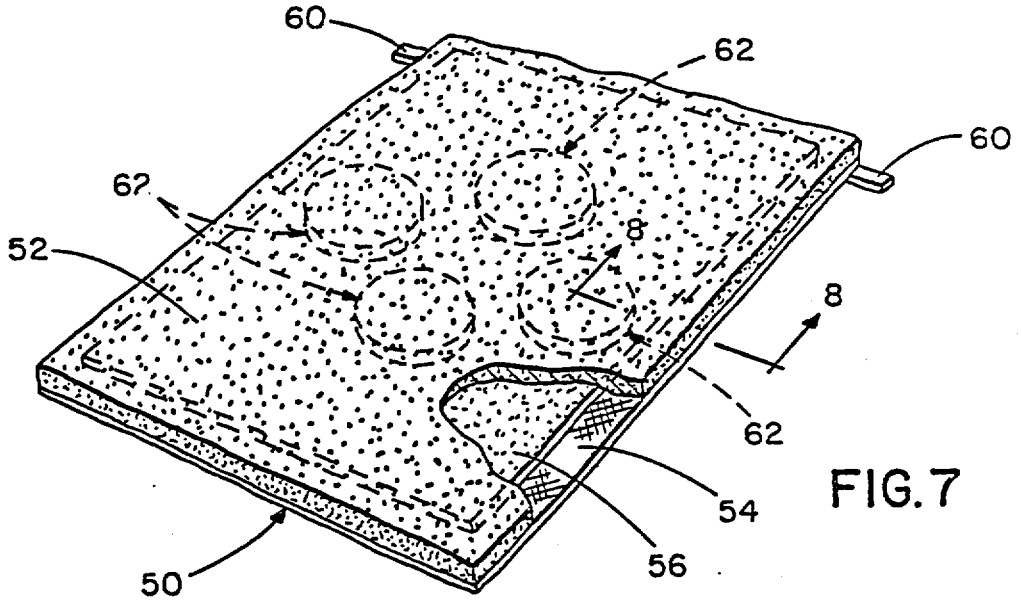
FIG. 7 is an enlarged perspective view of the diaper of a specific embodiment of the present invention.

While this invention is susceptible of embodiment in many different forms, there is shown in the drawings and will herein be described in detail preferred embodiments of the invention with the understanding that the present disclosure is to be considered as an exemplification of the principles of the invention and is not intended to limit the invention to the embodiments illustrated. The scope of the invention will be pointed out in the appended claims.

The diaper of the present invention is indicated in its entirety at 10 in FIG. 1, and is comprised of a first outer layer 12 which is moisture permeable and adapted to be positioned adjacent the skin of an infant, a second outer layer 14 which is moisture impermeable and adapted to be disposed outwardly and form a moisture barrier when the diaper is worn, and an absorbent layer or panel 16 which is disposed between layers 12 and 14 and which is adapted to absorb and contain liquid passing through facing layer 12 and retained by backing layer 14. In the illustrated embodiment layers 12, 14 and 16 are rectangular, with layers 12 and 14 being the same size and coterminous with one another, and with layer 16 being smaller than layers 12 and 14 and generally centered with respect thereto so that generally equally sized marginal portions of layers 12 and 14 extend beyond the sides and ends of layer 16, as can be best seen in FIG. 2.

As noted above, backing layer 14 is preferably formed of a thin thermoplastic sheet, such as embossed polyethylene, to impart strength to the diaper as well as providing a moisture barrier. During manufacturing of the diaper, a plurality of transversely spaced, longitudinally extending glue lines 18 are deposited on backing layer 14, and facing layer 12 is secured to backing layer 14 by glue lines that are positioned laterally outwardly of the side edges of panel 16, and by the ends of glue lines that extend outwardly beyond the ends of panel 16. Glue lines 18 in the central portion of the backing layer 14 retain the panel in fixed relation relative to the facing layer 12 and backing layer 14. As noted above, absorbent layer 16 is preferably formed from a batt of loosely compacted cellulosic fibers of papermaking length, and the surface of layer 16 adjacent backing layer 14 is preferably moistened and compacted during manufacture to provide a relatively dense, paper-like wicking layer having enhanced strength for securement to the backing layer.

The nature of the facing layer 12 is not critical to the present invention so long as it is moisture permeable, and it may be formed of generally hydrophobic non-woven fabrics mentioned above, or of a thermoplastic film having a multiplicity of fine apertures therein. In the latter case, glue lines 18 may be eliminated in whole or in part and the facing and backing layers may be heat sealed to one another. In some instances, as for example when the facing layer is an apertured non-woven fabric or a thermoplastic film having relatively large openings therein, in order to prevent fibers from the absorbent panel for dusting or linting through the facing layer, a moisture permeable layer, such as a high wet strength tissue layer, may be interposed between the facing and absorbent layer.

Tape closures 20 may be provided at one end of the diaper, and secured to the backing and/or facing layers for securing the diaper about the torso of an infant in the configuration shown in FIG. 1, as is well understood in the art.

In order to provide increased absorptive capacity as well as an increased rate of absorption, absorbent panel 16 has one or more cells or pockets 22 therein each of which includes a uniform admixture of discrete hydrocolloid particles 24 and discrete introfying particles 26. In accordance with the present invention, the hydrocolloid particles are dry, solid granules when the diaper is manufactured, having been ground or otherwise formed to maximize the exposed surface area of the hydrocolloid material. The hydrocolloid particles need not have the same size or shape, or chemical composition; since the present invention contemplates that blends of chemically different hydrocolloid materials may be utilized. However, as presently understood, it is desired that the hydrocolloid particles be chemically identical, and generally of the same size and shape.

The introfying particles 26 are physically separate from and not chemically or otherwise bound or joined to the hydrocolloid particles 24. Particles 26 are dry, solid granules that are blended and distributed in a uniform admixture with particles 24, and are present in sufficient quantity to segregate and separate the hydrocolloid particles from one another, even when the hydrocolloid particles swell and expand upon being wetted. The introfying particles contemplated by the present invention such as perlite and Celite mentioned above, have sufficient structural integrity to substantially retain their size and shape when subjected to compressive forces exerted by the swelling and expanding hydrocolloid particles. And, since the bulk volume of the admixture is substantially greater than the bulk volume of the hydrocolloid particles, the introfying particles function to preserve the interstices around the hydrocolloid particles thereby insuring liquid impinging upon the pockets 22 will have access to all of the hydrocolloid particles therein.

In the embodiment of FIGS. 1-3 four individually separate and distinct pocket 22 are provided in panel 16. The number, size, shape, location and spacing of the pockets 22 is not critical to the present invention, and a variety of different arrangements will be hereinafter described. However, each pocket is moisture-permeable, at least in part, so that liquid can have access to the contents of the pockets; and each pocket is constructed and arranged so that the hydrocolloid particles can expand relatively freely and distend the constraining walls of the pockets if necessary, without expanding into and thereby diminishing the absorptive capacity provided by the capillary network of fibrous panel 16.

With reference to FIGS. 3 and 3A, pockets 22 are illustrated as being disposed medially between the opposite faces of the panel. In this arrangement the lowermost portion of the panel, i.e., the portion below pockets 22 and adjacent backing layer 14 is deposited first, followed by placement of the pockets 22 and deposition of the portion of the panel above pockets 22. The present invention also contemplates that the pockets 22 may be deposited directly on backing sheet 14 during manufacture, and that the panel 16 may be air laid thereover. With this technique, it is possible to have one face of each pocket disposed in direct contact with the backing sheet and the opposite face either in direct contact with the facing sheet or separated therefrom by a thin fibrous overlay. In instances where it is contemplated that the pockets 22 be in direct contact with both the facing and backing layers, the panel may be separately formed and cut-out in the areas to receive the pockets 22, which may be inserted in a separate manufacturing step. The present invention also contemplates that pockets 22 containing hydrocolloid and introfying particles may be positioned between the panel 16 and the facing layer 12 and/or between the panel 16 and the backing layer 14.

In the embodiment of FIGS. 1–3 each pocket 22 is illustrated as being formed by a pair of sheet-like membranes 28. Membrances 28 are moisture pervious members having a pore size sufficient to permit entry of liquid, but small enough to prevent the hydrocolloid particles and introfying particles from escaping. illustratively the membrances 28 may be formed of the high wet strength, inherently heat-sealable Dexter tea bag paper mentioned, and such membranes may be heat sealed to one another around their perimeter, as is shown at 28a in FIG. 3. The present invention also contemplates the utilization of bags and pouches which may, for example, be formed by folding a single moisture permeable membrane upon itself and sealing facing surfaces together to form a closed cell or pocket.

While the embodiment of FIGS. 1–3 shows the pockets 22 as being spaced from one another, the present invention also contemplates the provision of a plurality of connected, yet independent and non-communicating pockets. Two of such arrangements are illustrated in FIGS, 4, 5 and 6, and identical reference characters are utilized in these views to designate those elements which correspond to like elements in the embodiment of FIGS. 1–3.

With specific reference to FIGS. 4 and 6, pocket means 30 is illustrated as being disposed medially of absorbent fibrous panel 16, which is sandwiched between facing layer 12 and backing layer 14. The facing, backing and absorbent layer may be of the type described above, and it will be noted from FIG. 6 that a wicking means in the form of densified, cellulosic, paper-like skin 32 is shown as being formed integrally on the surface of panel 16 adjacent backing layer 14.

Pocket means 30 is defined by a pair of thin flexible membranes 34 and 36 which have their facing surfaces secured to one another in a plurality of generally equally spaced perpendicularly disposed, longitudinally and transversely extending seal zones 38. As a result, pocket means 30 includes a plurality of longitudinally and transversely adjacent individual pockets 40 which are secured to one another, but which have their contents retained physically separate from one another. As is evident from FIGS. 4 and 6, pocket means 30 defines a quilt like member, and the entire diaper may be given a quilted appearance by passing it through the nip of embossing rolls to cause indentations 42 in the facing layer and 44 in the backing layer in alignment with the seal zones 38.

As with the previously described embodiment, membranes 34 and 36 are preferably inherently heat sealable for ease of manufacture. At least membranes 34 is moisture permeable, so that liquid passing through facing layer 12 and absorbed in panel 16 will have acess to the contents of pockets 40. In a simplified arrangement which eliminates membrane 36, pocket means 30 may be disposed between panel 16 and backing layer 14, in which case membrane 34 may be secured directly to backing layer 14, with the individual pockets being formed therebetween.

Referring now to FIG. 5, a further embodiment of a diaper having a quilted appearance is illustrated, with individual honeycomb-like cells 48 being defined between the intersections of sinuous sealing and embossing zones 46. It is believed that a wide variety of other interconnected yet non-communicating pocket arrangements will be readily apparent to those skilled in the art, and the arrangements of FIGS. 4–6 have been included for purposes of example only.

Figure 8:
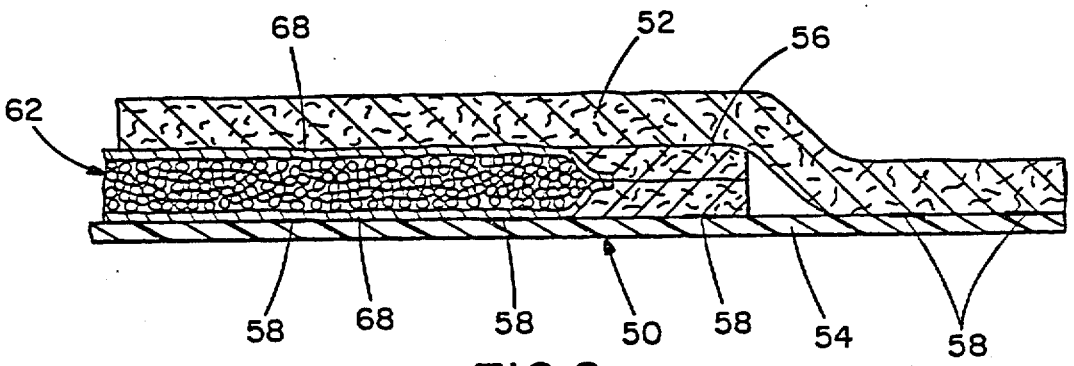
FIG. 8 is a cross-sectional view taken generally along Line 7—7 of FIG. 7.
Figure 9:
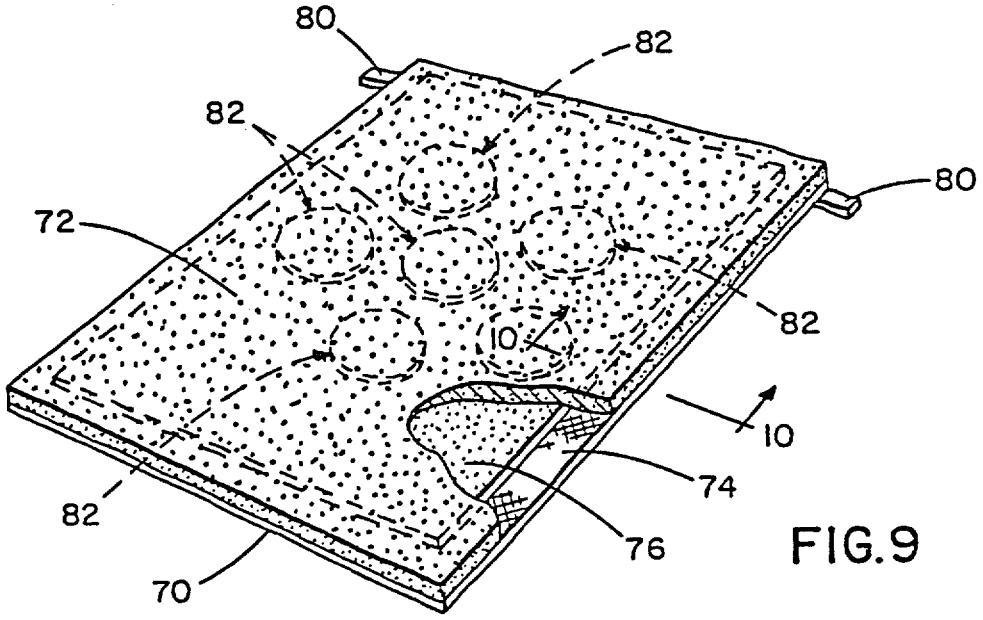
FIG. 9 is an enlarged perspective view of the diaper of another specific embodiment.
Figure 10:
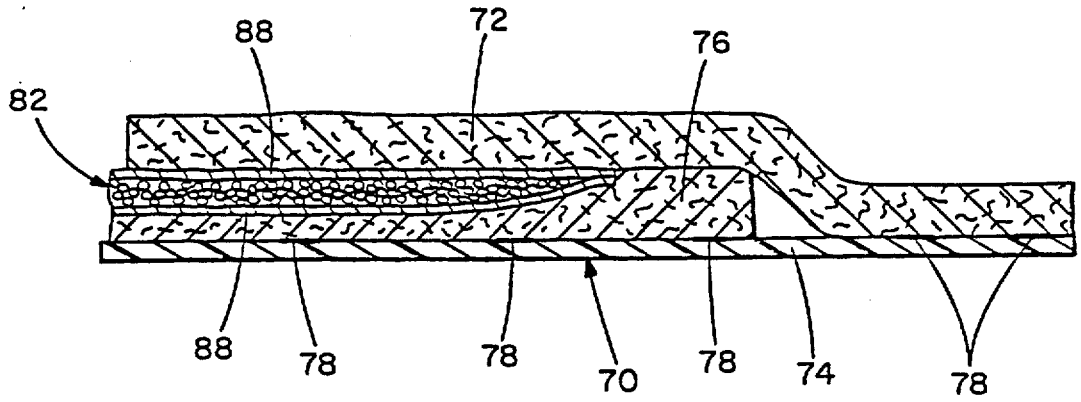
FIG. 10 is a cross-sectional view taken generally along Line 9—9 of FIG. 9.

Referring now to FIGS. 7 and 8, a further embodiment of a diaper 50 is illustrated with individual pockets 62 extending between the facing 52 and the backing 54. Each pocket includes hydrocolloid particles and introfying particles as shown in FIG. 3a. Each pocket 62 is formed by a sheet-like membrane 68. The membranes 68 are moisture pervious. An absorbent fibrous panel 56 surrounds the pockets 62 between the facing 52 and the backing 54. The absorbent panel 56 and the facing 52 are adhere to the backing by glue lines 58. Referring now to FIGS. 9 and 10 a further embodiment of a diaper 70 is illustrated with individual pockets 82 placed between the facing 72 and an absorbent fibrous panel 76. Each pocket 82 includes hydrocolloid particles and introfine particles as shown in FIG. 3a. Also each pocket 82 is formed by a sheet-like membrane 88. The membanes 88 are moisture-pervious. The absorbent panel 76 and the facing 72 are adhere to the backing 74 by glue lines 78.

Figure 11:
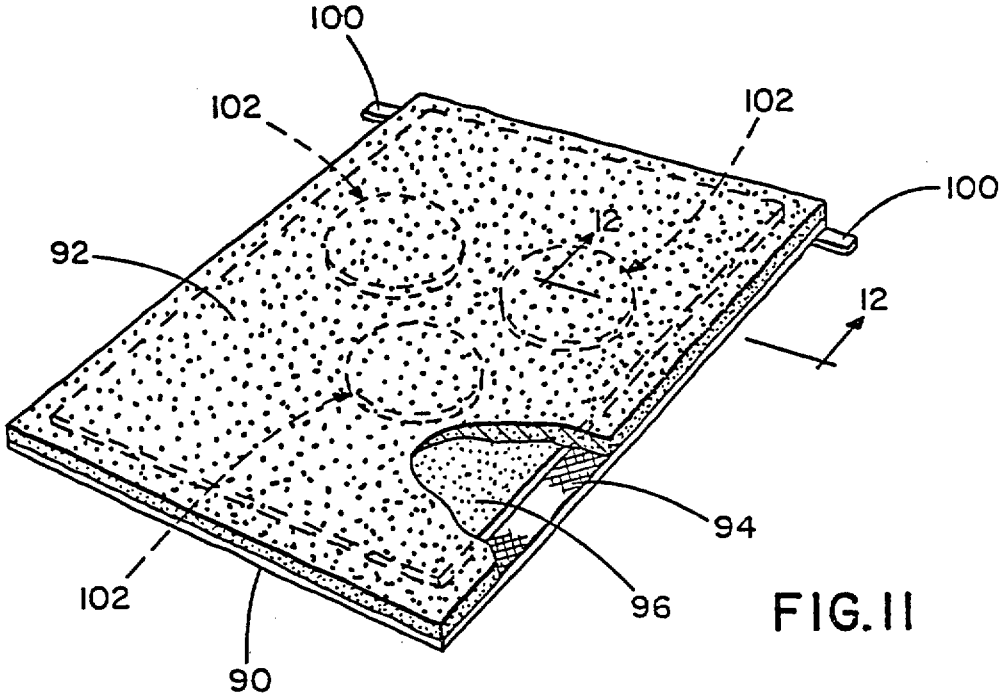
FIG. 11 is an enlarged perspective view of the diaper of a still further specific embodiment.
Figure 12:
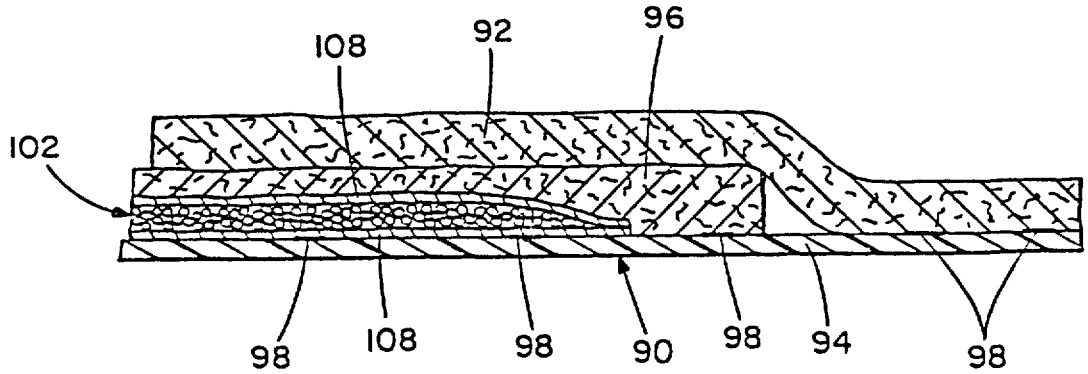
FIG. 12 is a cross-sectional view taken generally along Line 11—11 of FIG. 11.

Referring now to FIGS. 11 and 12, a further embodiment of a diaper 90 is illustrated with individual pockets 102 placed between an absorbent fibrous panel 96 and the backing 94. Each pocket 102 includes hydrocolloid particles and introfine particles as shown in FIG. 3a. Each pocket 102 is formed by a sheet-like membrane 108. The membranes 108 are moisture-pervious. The absorbent panel 96 and the facing 92 are adhere to the backing 94 by glue lines 98.

In FIGS. 7, 9, and 11 the diapers are secured by tape tabs 60, 80, and 100, respectively.

As is set forth above, each of the pockets associated with the absorbent panels of the various diapers contemplated herein contains a uniform admixture of discrete hydrocolloid particles and introfying particles, with the particles of the admixture being present in a bulk volume range of from about 4 to about 60 times the bulk volume of the hydrocolloid particles themselves, and with the particles of the admixture preferably being present in a bulk volume range of from about 20 to about 50 times the bulk volume of the hydrocolloid particles themselves. In each of the disclosed arrangments, the hydrocolloid and introfying particles occupy only a portion of the internal volume of the individual pockets, so that the hydrocolloid particles can expand without rupturing the walls of the individual pockets. The present invention also contemplates that the walls or membranes of the individual pockets may be capable of expansion, such as by pleating or creping the materials from which the pockets are formed.

With pockets of the type described above, when the hydrocolloid particles are wetted and begin to swell, they expand to substantially fill the internal volume of the individual pockets, after which the individual pockets themselves may expand. The expanding walls will push the adjacent fibers of the batt aside, but the swelling hydrocolloid particles will remain trapped within the pockets and will not occupy the capillary voids of the fibrous panel. As a result the total absorptive capacity of the diaper is significantly increased. Since the unique pocket arrangement of the present invention significantly improves the total absorptive capacity of the diaper, a lesser amount of fibrous material may be used for a diaper of a given desired absorptive capacity, with the result that the dry diaper is less bulky and more comfortable to the infant.

While the present invention has been described in detail with respect to a diaposable diaper, the present invention should be considered as being applicable to absorbent articles generally, unless indicated to the contrary in the appended claims.

I claim:

1. An absorbent article comprising a moisture-permeable first outer layer, an absorbent layer adjacent said outer layer, said absorbent layer including at least one discrete pocket therein, at least a portion of said pocket being moisture permeable, said pocket containing therewithin a substantially dry uniform admixture of discrete particulate water-insoluble hydrocolloid material and discrete water-insoluble introfying paticles, each of said introfying particles being physically separate from and not chemically or otherwise bound or joined to any of the hydrocolloid particles and which introfying particles maintain the particles of hydrocolloid material in spaced relationship relative to one another, and introfying particles having sufficient structural integrity to substantially retain their size and shape when subjected to compressive forces exerted by said hydrocolloid particles as they swell and expand when wetted and a second outer layer at the side of said absorbent layer opposite from said first outer layer.

2. An absorbent article as set forth in claim 1 wherein said absorbent layer includes a plurality of discrete pockets each containing an admixture of hydrocolloid and introfying particles.

3. An absorbent article as set forth in claim 2 wherein said absorbent layer includes a cellulosic fibrous batt of loosely compacted fibers adjacent to said pockets.

4. An absorbent article as set forth in claim 1 wherein said second outer layer is moisture impermeable.

5. An absorbent article as set forth in claim 1 wherein said absorbent article is a diaper, said first and second layers being coterminous and secured to one another, and said absorbent layer being smaller than said first and second outer layers and disposed inwardly of the periphery thereof.

6. A disposable diaper comprising a moisture-permeable facing layer, a moisture-impermeable backing layer, and an absorbent panel sandwiched between said facing and backing layers, said absorbent panel being a cellulosic fibrous batt of loosely compacted fibers and including a plurality of discrete pockets therein, at least a portion of each of said pockets being moisture permeable, and each of said pockets containing therewithin a substantially dry uniform admixture of discrete particles of water-insoluble hydrocolloid material and discrete water-insoluble introfying particles, each of said introfying particles being physically separate from and not chemically or otherwise bound or joined to any of said hydrocolloid particles, said particles of hydrocolloid material being retained in spaced relationship relative to one another by said discrete water-insoluble introfying particles disposed within each pocket, said introfying particles having sufficient structural integrity to substantially retain their size and shape when subjected to compressive forces exerted by said hydrocolloid particles as they well and expand when wetted.

7. A disposable diaper as set forth in claim 6 wherein said pockets are spaced from one another.

8. A disposable diaper as set forth in claim 6 wherein said pockets are interconnected.

9. A disposable diaper as set forth in claim 6 wherein each pocket includes a moisture permeable membrane surrounding said hydrocolloid and introfying particles.

10. A disposable diaper as set forth in claim 6 wherein said absorbent layer includes wicking means on the face thereof adjacent said moisture impermeable layer.

11. A disposable diaper as set forth in claim 10 wherein said wicking means is integral with said batt and comprised of a densified, compacted, porous, absorbent fibrous region having relatively high cohesive strength, relatively good capillarity, relatively good shape and volume stability and relatively high fluid retentivity.

12. A disposable diaper as set forth in claim 6 wherein said fibrous batt includes a plurality of openings extending between said facing and backing layers, each opening having a pocket therein.

13. A disposable diaper as set forth in claim 6 wherein said pockets are disposed between said facing layer and fibrous batt.

14. A disposable diaper as set forth in claim 6 wherein said pockets are disposed between said fibrous batt and backing layer.

15. An absorbent article comprising a moisture permeable facing layer, a backing layer, and an absorbent panel sandwiched between said facing and backing layers, said absorbent panel including at least one discrete pocket therein, at least a portion of said pocket being moisture permeable, and said pocket containing therewithin a plurality of substantially dry discrete particles of water-insoluble hydrocolloid material, said particles of hydrocolloid material being retained in spaced relationship relative to one another by discrete water-insoluble introfying particles disposed within said pocket, each of said introfying particles being physically separate from and not chemically or otherwise bound or joined to any of said hydrocolloid particles, said hydrocolloid particles and said introfying particles being present in said pocket in a uniform admixture which has a bulk volume from about 4 to 60 times as great as the bulk volume of said hydrocolloid particles therein.

16. An absorbent article comprising a moisture permeable facing layer, a backing layer, and an absorbent panel sandwiched between said facing and backing layers, said absorbent panel including at least one discrete pocket therein, at least a portion of said pocket being moisture permeable, and said pocket containing therewithin a plurality of substantially dry discrete particles of hydrocolloid material, said particles of hydrocolloid material being retained in spaced relationship relative to one another by discrete introfying particles disposed within said pocket, each of said introfying particles being physically separate from and not chemically or otherwise bound or joined to any of said hydrocolloid particles, said introfying particles having sufficient structural integrity to substantially retain their size and shape when subjected to compressive forces exerted by said hydrocolloid particles as they swell and expand when wetted, said hydrocolloid particles and said introfying particles being present in said pocket in a uniform admixture which has a bulk volume from about 4 to about 60 times as great as the bulk volume of the hydrocolloid particles therein.

17. An absorbent article as set forth in claims 16 wherein said hydrocolloid and introfying particles occupy only a portion of internal volume of said pocket.

18. An absorbent article as set forth in claim 16 wherein at least a portion of said pocket is defined by an expansible membrane.

19. An absorbent article as set forth in claim 16 wherein said pocket is formed by a bag formed of a porous, high wet strength, light-weight filter paper.

20. An absorbent article as set forth in claim 19 wherein said bag is formed of two sheets of filter paper secured to one another round their periphery.

21. An absorbent article as set forth in claim 16 wherein said introfying particles have a bulk density less than about 0.05 gr./ml.

22. An absorbent article as set forth in claim 16 wherein said bulk volume of said uniform admixture is from about 20 to about 50 times the bulk volume of the hydrocolloid particles therein.

*23. An absorbent panel structure for an absorbent article, comprising:*

*an absorbent layer comprising loosely compacted cellulosic fibrous material; and*

*pocket means provided within said absorbent layer medially of upper and lower portions of said loosely compacted cellulosic fibrous material of said absorbent layer, said pocket means comprising discrete individual pockets of superabsorbent hydrocolloid material,*

*said upper and lower portions of said absorbent layer being embossed toward each other throughout the thickness of each of said upper and lower portions, at embossed areas,*

*said pockets of hydrocolloid material being spaced and physically separated from each other by said embossed area between adjacent ones of said pockets.*

*24. An absorbent panel structure in accordance with claim 23, including*

*a densified, paper-like wicking layer comprising cellulosic fibrous material formed integrally with said absorbent layer at a surface of one of said upper and lower portions of said absorbent layer.*

*25. An absorbent panel structure in accordance with claim 24, wherein*

*said densified wicking layer is provided at one of the outer surfaces of said absorbent layer.*

*26. An absorbent panel structure in accordance with claim 25, wherein*

*said densified wicking layer is provided at the outer surface of the lower portion of said absorbent layer.*

*27. An absorbent panel structure in accordance with claim 23, including*

*a plurality of said embossed areas arranged in spaced, parallel relation to each other.*

*28. An absorbent panel structure in accordance with claim 27, including*

*at least one of said embossed areas extending perpendicularly to said parallel ones of said embossed areas.*

*29. An absorbent panel structure in accordance with claim 28, including*

*a plurality of said embossed areas extending in spaced apart, perpendicular relation to said parallel ones of said embossed areas.*

*30. An absorbent panel structure in accordance with claim 23, wherein*

*said discrete pockets of superabsorbent hydrocolloid material are each bound by said embossed areas of said upper and lower portions of said absorbent layer.*

*31. An absorbent panel structure in accordance with claim 23, including*

*a moisture-permeable facing layer, and a moisture-impermeable backing layer, said absorbent layer and said pocket means being sandwiched between said facing layer and said backing layer.*

*32. An absorbent panel structure for an absorbent article, comprising:*

*an absorbent layer comprising absorbent loosely compacted fibrous material; and*

*superabsorbent hydrocolloid material positioned within said absorbent layer medially of upper and lower portions of said loosely compacted fibrous material of said absorbent layer,*

*said absorbent panel structure comprising means for retaining said superabsorbent hydrocolloid material in position medially of said upper and lower portions of said absorbent layer including embossed areas at which said upper and lower portions of said absorbent layer are embossed toward each other throughout the thickness of each of said upper and lower portions.*

*33. An absorbent panel structure in accordance with claim 32, including*

*a plurality of said embossed areas arranged in spaced parallel relation to each other.*

*34. An absorbent panel structure in accordance with claim 33, including*

*at least one of said embossed areas extending transversely of said spaced parallel ones of said embossed areas.*

*35. An absorbent panel structure in accordance with claim 34, including*

*a plurality of said embossed areas extending transversely of said spaced parallel ones of said embossed areas.*

*36. An absorbent panel structure in accordance with claim 32, including*

*a densified wicking layer comprising fibrous material formed integrally with said absorbent layer at a surface of one of said upper and lower portions of said absorbent layer.*

*37. An absorbent panel structure for an absorbent article, comprising:*

*an absorbent layer comprising loosely compacted cellulosic fibrous material; and*

*pocket means provided within said absorbent layer medially of upper and lower portions of said loosely com-*

*pacted cellulosic fibrous material of said absorbent layer, said pocket means comprising discrete individual pockets of superabsorbent hydrocolloid material,*

*said upper and lower portions of said absorbent layer being embossed toward each other, throughout the thickness of each of said upper and lower portions, at embossed areas,*

*said pockets of hydrocolloid material being spaced and physically separated from each other by said embossed area between adjacent ones of said pockets,*

*wherein said pocket means includes fluid permeable membrane means for containing said individual pockets of hydrocolloid material.*

*38. An absorbent panel structure in accordance with claim 37, wherein*

*each said individual pocket comprises an admixture of said hydrocolloid material and discrete water-insoluble introfying particles.*

*39. An absorbent panel structure for an absorbent article, comprising:*

*an absorbent layer comprising absorbent loosely compacted fibrous material; and*

*superabsorbent hydrocolloid material positioned within said absorbent layer medially of upper and lower portions of said loosely compacted fibrous material of said absorbent layer,*

*said absorbent panel structure comprising means for retaining said superabsorbent hydrocolloid material in position medially of said upper and lower portions of said absorbent layer including embossed areas at which said upper and lower portions of said absorbent layer are embossed toward each other, throughout the thickness of each of said upper and lower portions,*

*wherein said retaining means comprises fluid permeable membrane means for containing said superabsorbent material in discrete individual pockets.*

*40. An absorbent panel structure in accordance with claim 39, wherein*

*each said individual pocket comprises an admixture of said superabsorbent material and discrete water-insoluble introfying particles.*

* * * * *